United States Patent
Laymon et al.

[11] Patent Number: 6,096,022
[45] Date of Patent: *Aug. 1, 2000

[54] BI-DIRECTIONAL CATHETER

[75] Inventors: Jonathan A. Laymon, San Francisco; Michael J. Mariant, San Jose; Robert Hergenrother, Union City; James C. Peacock, III, Saratoga, all of Calif.

[73] Assignee: Target Therapeutics Inc., Fremont, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/522,746

[22] Filed: Aug. 31, 1995

[51] Int. Cl.$^7$ .................................................. A61M 25/00
[52] U.S. Cl. ............................................ 604/523; 604/533
[58] Field of Search .................................. 604/103, 104, 604/158, 164, 264, 280, 281–283, 905, 523, 533, 538

[56] References Cited

U.S. PATENT DOCUMENTS

| | | |
|---|---|---|
| 2,009,393 | 7/1935 | Failla . |
| 3,382,865 | 5/1968 | Worrall, Jr. . |
| 3,628,813 | 12/1971 | Lee . |
| 3,976,311 | 8/1976 | Spendlove ................................ 285/12 |
| 3,977,403 | 8/1976 | Patel ...................................... 128/221 |
| 4,068,659 | 1/1978 | Moorehead . |
| 4,166,469 | 9/1979 | Littleford . |
| 4,243,050 | 1/1981 | Littleford . |
| 4,345,606 | 8/1982 | Littleford . |
| 4,390,017 | 6/1983 | Harrison et al. ....................... 604/270 |
| 4,411,055 | 10/1983 | Simpson et al. . |
| 4,449,532 | 5/1984 | Storz . |
| 4,451,256 | 5/1984 | Weikl et al. . |
| 4,509,944 | 4/1985 | King et al. . |
| 4,551,146 | 11/1985 | Rogers ................................... 604/403 |
| 4,581,025 | 4/1986 | Timmermans . |
| 4,596,559 | 6/1986 | Fleischhacker . |
| 4,739,768 | 4/1988 | Engleson . |
| 4,772,266 | 9/1988 | Groshong . |

(List continued on next page.)

FOREIGN PATENT DOCUMENTS

| | | |
|---|---|---|
| 0343520 | 11/1989 | European Pat. Off. . |
| 2146405 | 4/1985 | United Kingdom . |

OTHER PUBLICATIONS

Argyle; "The Standard Of Excellence In Medical Surgical Tubes and Catheters"; Received on Oct. 12, 1964, p. 8.
Argyle; "A New Standard Of Excellence In Medical, Surgical Tubes and Catheters"; Dec. 20, 1960, pp. 1–12.
Lexis Printout of U.S. Patent No. 4,411,055 to Simpson et al., (Oct. 25, 1983).
Lexis Printout of U.S. Patent No. 4,616,652 to Simpson (Oct. 14, 1986).
Lexis Printout of U.S. Patent No. 4,669,469 to Gifford, III et al., (Jun. 2, 1987).
Lexis Printout of U.S. Patent No. 4,781,186 to Simpson et al., (Nov. 1, 1988).
Lexis Printout of U.S. Patent No. 4,926,858 to Gifford, III et al., (May 22, 1990).
Lexis Printout of U.S. Patent No. 5,047,040 to Simpson et al., (Sep. 10, 1991).
Lexis Printout of U.S. Patent No. 5,053,044 to Mueller et al., (Oct. 1, 1991).
Lexis Printout of U.S. Patent No. 5,092,873 to Simpson et al., (Mar. 3, 1992).

*Primary Examiner*—Corrine McDermott
*Assistant Examiner*—Cris L. Rodriguez
*Attorney, Agent, or Firm*—Morrison & Foerster II

[57] ABSTRACT

This is a percutaneous medical device and related methods for its use. More particularly, it is a percutaneous catheter having ends which are interchangeably capable both of distal introduction into a delivery device lumen or body space and of proximal coupling to other medical devices.

16 Claims, 9 Drawing Sheets

U.S. PATENT DOCUMENTS

| | | | |
|---|---|---|---|
| 4,819,637 | 4/1989 | Dormandy, Jr. et al. | |
| 4,917,094 | 4/1990 | Lynch et al. | |
| 4,941,874 | 7/1990 | Sandow et al. | |
| 4,983,168 | 1/1991 | Moorehead | |
| 4,994,069 | 2/1991 | Ritchart et al. | |
| 5,047,040 | 9/1991 | Simpson et al. | |
| 5,098,392 | 3/1992 | Fleischhacker et al. | |
| 5,122,136 | 6/1992 | Guglielmi et al. | |
| 5,133,731 | 7/1992 | Butler et al. | |
| 5,139,032 | 8/1992 | Jahrmarkt et al. | 128/772 |
| 5,167,624 | 12/1992 | Butler et al. | |
| 5,203,771 | 4/1993 | Melker et al. | |
| 5,226,911 | 7/1993 | Chee et al. | |
| 5,228,452 | 7/1993 | Samson | |
| 5,234,437 | 8/1993 | Sepetka | |
| 5,250,071 | 10/1993 | Palermo | |
| 5,261,916 | 11/1993 | Engelson | |
| 5,263,945 | 11/1993 | Byrnes et al. | 604/283 |
| 5,273,042 | 12/1993 | Lynch et al. | |
| 5,304,142 | 4/1994 | Liebl et al. | |
| 5,312,377 | 5/1994 | Dalton | 604/283 |
| 5,312,415 | 5/1994 | Palermo | |
| 5,330,435 | 7/1994 | Vaillancourt | 604/167 |
| 5,336,205 | 8/1994 | Zenzen et al. | |
| 5,342,394 | 8/1994 | Matsumo et al. | |
| 5,348,542 | 9/1994 | Ellis | |
| 5,366,444 | 11/1994 | Martin | |
| 5,382,259 | 1/1995 | Phelps et al. | |
| 5,382,260 | 1/1995 | Dormandy, Jr. et al. | |
| 5,405,339 | 4/1995 | Kohnen et al. | 604/283 |
| 5,476,472 | 12/1995 | Dormandy, Jr. et al. | |
| 5,478,331 | 12/1995 | Heflin et al. | 604/283 |
| 5,490,503 | 2/1996 | Hollister | 128/205.12 |
| 5,505,710 | 4/1996 | Dorsey, III | 604/158 |
| 5,514,117 | 5/1996 | Lynn | 604/283 |
| 5,540,464 | 7/1996 | Picha | 285/328 |

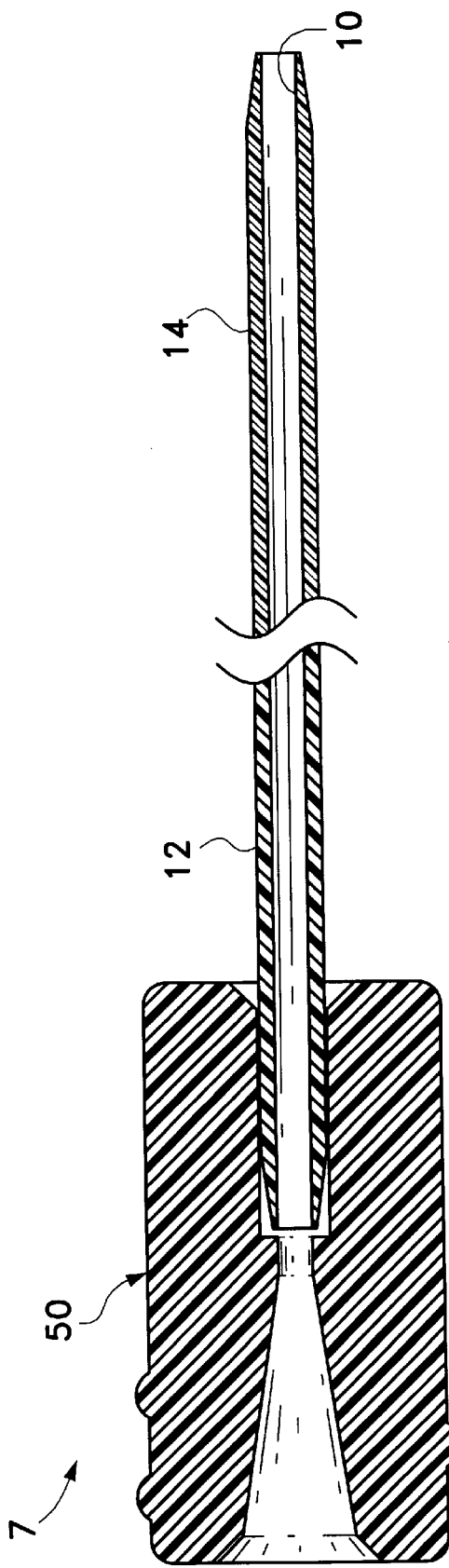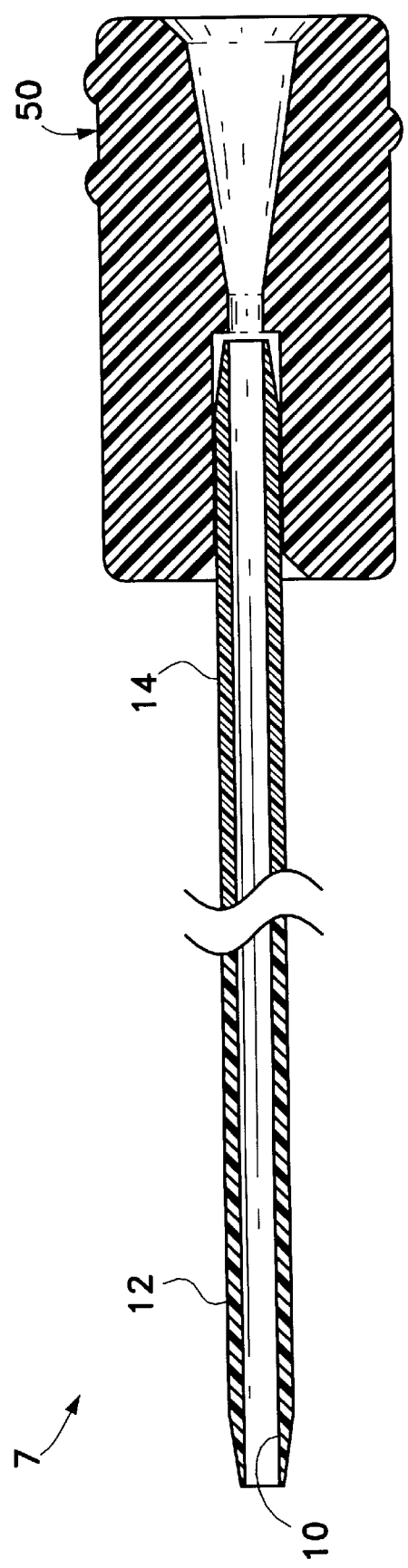

BI-DIRECTIONAL CATHETER

FIELD OF THE INVENTION

This invention relates to a percutaneous medical device and related methods of use. More particularly, it relates to a percutaneous catheter having both ends interchangeably capable of distal introduction into a delivery device lumen or body space and of proximal coupling to other medical devices.

BACKGROUND OF THE INVENTION
Uni-Directional Catheter Overview

Many different medical treatments are facilitated by the use of percutaneous catheterization devices and techniques. Percutaneous catheterization techniques generally involve introducing catheters as object devices, such as diagnostic or treatment devices, into the vasculature or other internal biological locations through delivery devices. As such, we refer to a device as a "delivery device" when it facilitates the placement of another device or treatment modality at a desired location. Similarly, we refer to a device as an "object device" when it is the device to be delivered through or by a delivery device.

Most catheterization treatments involve common vascular access techniques. Generally, an initial puncture is made in a desired initial access vessel by a needle. A guide wire is then inserted through the internal bore of the needle and out of the needle's end into the vessel lumen. Next the needle is withdrawn while the wire is held in place in the vessel. A dilator device is threaded over the wire and through the puncture site to increase the hole diameter to appropriate dimensions for delivery and object devices to be placed therethrough. The dilator is then removed over the wire, with the wire still in place in the vessel.

Next, a vascular access introducer sheath is threaded over the wire and into the vessel. The wire is removed and the introducer sheath is left in place as a delivery device to provide co-axial access into the vascular tree wherein catheters, guidewires, and other object devices can be placed therethrough for treatment. Radiopaque materials are generally provided on these object devices for X-Ray visualization during in-vivo placement.

"Catheters" are generally elongated devices with two elongate end portions. For known catheter designs, each elongate end portion is generally adapted for a specific function distinct from the other end portion, e.g., one end for introduction into a body and the other end for connection to another piece of medical equipment. Conduit lumens often extend between the elongate end portions.

Catheters can serve dual roles as delivery devices and as object devices. They are used as delivery devices when equipped with a conduit lumen to facilitate the delivery of a fluid or another device, and may also be object devices when the catheter's placement at a desired in-vivo location is facilitated by a separate delivery device. Multiple catheters may be arranged in a telescoping co-axial arrangement with several of those catheters performing dual delivery device/object device roles. Percutaneous methods for delivering a particular object device for remote in-vivo treatment often employ such a telescoping arrangement.

Catheters often comprise a first catheter end portion that is a "catheter distal end" for placement into a patient's body space or into another device lumen leading to such a body space. At least one end hole or side hole port is usually provided on the catheter distal end to allow communication between the internal catheter lumen and the distal body space that houses the distal end portion. The catheter distal end is usually adapted to be an object device in the sense that it may be delivered to a desired site through a conduit delivery device or over a rail delivery device. Thus, very flexible materials are chosen to track through the tortuosities of distal body spaces. The catheter distal end is also adapted to be a delivery device when a lumen is provided such that another device can be delivered therethrough. Thus, materials and other design features, such as distal tip shape, may be chosen to optimize support that the catheter distal end can give for the delivery of the object device therethrough.

The second catheter end portion is generally the "catheter proximal end" that is closest to the physician and is generally adapted to receive or couple with another device or to be manipulated by the physician. Luer adaptors or couplers are often provided on the catheter proximal end for interfacing with other devices. Object devices to be delivered through the catheter are received into a lumen at the proximal end portion, often being guided therein by a proximal coupler. A proximal luer fitting may also be provided to engage a syringe or other fluid delivery means. Proximal end portion materials are often chosen to accommodate relatively straight, larger bore vasculature of the proximal anatomy, wherein this section resides during in-vivo use. The special features particular to the catheter proximal end also combine to accommodate physician manipulation during handling and use.

Thus, catheters known in the art are designed for "uni-directional" use. Each of two catheter body end portions is designed to meet a specific and distinct proximal or distal need, and is thus generally not designed to be interchangeable with the other. However, patient dependent anomalies such as disease states or anatomy may require different designs of a particular catheter type. Since only uni-directional devices are available, such different design requirements are most usually met by making available multiple designs of the same type of catheter. An alternative of providing bi-directional delivery catheters having interchangeable ends for variable proximal or distal use has not heretofore been known. Examples of the uni-directional design of known catheters include dilators, distal delivery catheters such as microcatheters and infusion catheters, and proximal delivery devices such as introducer sheaths and cartridges.

Uni-Directional Dilators

Dilators are generally catheters used to dilate a hole initially made in a vessel to enlarge the hole's diameter and so allow for device access through the enlarged hole and into the internal lumen. Dilators have a tapering outer profile at a distal end. The dilator's proximal end is often adapted with a coupler for interfacing with other devices. Dilators are adapted so that the reduced profile tip enters the initial needle puncture hole with relative ease. Advancing the increasing diameter of the dilator's taper through the hole forces the tissue defining the hole to stretch or controllably tear in order to accommodate the larger bore regions of the dilator. Removing the dilator thereafter leaves an access hole into the artery of desired diameter.

One example of a dilator and related method of use in catheterization procedures is disclosed in U.S. Pat. No. 5,098,392 to Fleischhacker et al. Fleischacker et al. discloses a dilator and introducer sheath locking system made up of a dilator containing an elongated dilator cannula with a tapered distal end, a gripping clamp secured to its proximal end and a peel-away introducer sheath with a tapered distal end and a proximal end containing a splittable handle. The splittable handle interacts with the gripping clamp of the dilator to prevent undesired rearward migration of the dilator within the introducer sheath. The dilator has a tapered distal end and a luer fitting is attached to the proximal end for use in combination with other medical instruments and as a support during insertion of the introducer set. Every component of this system, including the dilator itself, is uni-directional.

Where large bore access sites are required, a series of dilators may be required to increase the bore in a step-wise manner. It is believed that gradual widening of the puncture site through gradual tapers and/or step-wise use of multiple dilators minimizes the trauma and tearing of tissue from the spreading action when compared to a more abrupt dilation. For a given taper pitch, ideally chosen for desirably minimized traumaticity, larger desired access holes require longer axial lengths of the dilator to be advanced beyond the puncture site. However, the available anatomy for the distal advancement of the dilator may be limited in a particular case, based upon patient dependent anomalies such as disease or tortuosity. Where distal advancement of the dilator is an issue, and where large diameter access hole is needed, multiple dilators of varying diameters may be required.

Uni-Directional Delivery Catheters

While known dilators are uni-directional catheters for widening an access hole to initiate percutaneous catheterization procedures, known delivery catheters are also uni-directional and are placed percutaneously through the access hole as object devices to facilitate the delivery of treatment devices or other modalities. Delivery catheters may be designed to deliver object devices or other treatments either in remote distal anatomy or in more proximal anatomy that is closer to the initial access site.

Delivery devices adapted to be used in distal anatomy are often delivered to a desired distal location as an object device over a rail or through another delivery device. Object devices or fluids can then be introduced into a proximal port and delivered distally via a lumen, then out of a distal port and into the distal site. A proximal coupler such as a funnel introducer and/or luer adaptor is generally provided on one end for interfacing with other devices.

The uni-directional nature of known delivery catheter designs, although desirably efficacious for particular categories of device uses, may require multiple designs of a single type of device in order to accommodate patient dependent performance requirements. For instance, a delivery catheter having a highly flexible distal end for superior trackability in distally tortuous anatomy may not have enough structural support to allow efficacious delivery of an object device therethrough for some treatments, such as when a guidewire extends beyond the delivery device and must push through a totally occluded vessel. Where the anatomy does not require the level of trackability for which the delivery catheter is designed, yet requires more support, it may be desirable for the distal portion of the delivery catheter to be more stiff and supportive. In fact, for certain sub-categories of uses, the desired performance of the distal end may require features closer to those provided on the proximal end. However, the proximal end can not be interchangeably adapted to become the distal end in a uni-directional design.

Other distal delivery catheter design features, e.g. tip shapes, may also be desirable for particular sub-categories of uses, but not for others. Thus, there are many reasons that multiple designs may be required of a given type of uni-directional delivery catheter.

One example of a uni-directional microcatheter for delivering fluids such as radiopaque agents, vaso-occlusive agents, or pharmacological agents is described in U.S. Pat. No. 4,739,768 to Engelson. Engelson describes a microcatheter having a relatively stiff proximal segment dimensioned to track a guide wire from an access site to a region adjacent the internal tissue. A fitting is attached to the proximal segment, such as a standard syringe fitting for use in connecting a syringe to the catheter for fluid injection. The distal portion of the device is relatively flexible and is dimensioned to be tracked co-axially over a guidewire rail along the tortuous path within soft tissue. A radiopaque band is located at the distal end as a marker for radiographically assisted positioning of the catheter in-vivo.

Another example of an infusion catheter with an elongate tubular body having proximal and distal ends and a lumen extending therebetween is disclosed in U.S. Pat. No. 5,336,205 to Zenzen et al. Zenzen discloses a flow-directed catheter made up of an elongate tubular body formed of relatively stiff tapered proximal segment, a relatively flexible and strong distal segment, and a transition section of relatively intermediate stiffness. The proximal segment uses a tapered proximal section for attachment to a proximal end fitting for adapting the catheter to a syringe. Blood flow directs the flexible distal segment to the target site.

Much like distal delivery devices, other delivery devices adapted for more proximal uses also have uni-directional designs optimized for a particular use. However, also like known delivery devices, sub-categories of uses have required that multiple introducer designs be available to make up for the relatively inflexible uni-directional designs. A desirable alternative of providing bi-directional introducer devices with variably interchangeable design features on opposite catheter ends has not heretofore been made available. Examples of uni-directional proximal delivery devices are access introducer sheaths or cannulas, and pre-loaded implant introducer cartridges.

One example of an introducer device for introducing object devices into body vessels is disclosed in U.S. Pat. No. 5,098,392 to Fleischhacker et al. (discussed above). Fleischhacker discloses a peel-away introducer sheath for use with a dilator. The introducer sheath has a tapered distal end and a proximal end containing a splittable handle which interacts with the gripping clamp of the dilator to prevent undesired rearward migration of the dilator within the introducer sheath. If a variation of the distal tip shapes or taper geometry or material flexibility were required for a sub-category of use for this sheath, a second sheath would be required imparting the desired feature or features on the uni-directional introducer sheath's distal end portion.

Introducer catheters for introducing object devices into other delivery devices have more pronounced limitations associated with known uni-directional designs. Particularly of interest are introducer devices configured as cartridges that house pre-loaded implantable devices. Such cartridges have been found to be particularly useful for introducing certain types of vaso-occlusive coils into distal delivery catheters, which provide for distal delivery of such coils to a desired vessel or aneurysm site for artificial occlusion. For certain vaso-occlusion coils having variable properties at opposite coil ends, varied distal/proximal orientations of the internally housed coils may be desired to optimize the features of the coil ends for occlusion of a chosen site. To allow for such variable coil orientations during delivery, multiple pre-loaded uni-directional cartridges may be required.

Vaso-Occlusion Coils & Uni-Directional Delivery Methods

Various types of vaso-occlusion coil devices and related methods are known, primarily including detachable coils and non-detachable coils. Known introducer devices and delivery techniques for these coils are uni-directional.

One type of vaso-occlusion coil apparatus is the detachable vaso-occlusion coil. This type of coil is generally detachably integrated at its proximal end with an elongate pusher and is delivered to a desired location for occlusion, by means of the pusher, through a delivery catheter which terminates at or near the entrance zone of the desired location. Once the coil is extended out of the delivery catheter and into the desired location, the coil is detached from the pusher and left as an implant. The detachment means may be mechanical, such as the type described in U.S. Pat. No. 5,250,071 to Palermo, or may be electrolytic, such as the type described in U.S. Pat. No. 5,122,136 to Guglielmi et al. Detachable coils of the type disclosed in these references are necessarily uni-directional since the pusher mechanism is integrated with the proximal side of the coil prior to insertion.

Other types of vaso-occlusion coils are not integrated with a pusher but are independent devices. Such coils are generally pre-packaged in pre-loaded introducer catheters as cartridges and discharged therefrom into a distal delivery catheter. Either a separate pusher forces the coil out the distal end of the cartridge or pressurized fluid hydraulically delivers the pre-loaded implant. Such coils can only be delivered in one direction because the known introducer cartridges within which they are pre-loaded are uni-directional.

One type of non-detachable vaso-occlusion coil assembly that is not integral with a pusher is disclosed in U.S. Pat. No. 5,382,260 for "Embolization Device and Apparatus Including an Introducer Cartridge and Method for Delivering the Same," to Dormandy, et al. (introduced infra). The Dormandy '260 patent discloses an introducer cartridge having a distal extremity with a tapered tip and a hub mounted on a proximal extremity. The cartridge is introduced into a coil delivery catheter in a catheter system as described earlier, and a stylet is used to push the embolization device out of the introducer cartridge into a passage in the coil delivery catheter. A guide wire is then used to push the coil through the coil delivery catheter until it advances beyond the tip thereof and into the desired site for occlusion.

Another non-detachable vaso-occlusion coil that is pre-loaded in an introducer cartridge for delivery is disclosed in U.S. Pat. No. 5,382,259 to Phelps et al. Phelps discloses a vaso-occlusion coil that may be continuous or segmented, onto which a fibrous, woven or braided, tubular covering or element is attached. Phelps further discloses that the coil devices may be supplied prepackaged in a sterile cannula which is adapted to engage the proximal end of a delivery catheter.

To deliver the Phelps et al. coil device, the distal end of a delivery catheter is placed adjacent to a desired occlusion site, and the coil-containing cannula is placed into engagement with the proximal end of the catheter. The coils are then transferred from the cannula lumen into the catheter lumen by exerting a force on the proximal end of the coil. A flexible pusher device then is used to push the coil through the delivery catheter and out its distal end to the desired site.

Phelps et al. also indicates that the vaso-occlusion coils as having varying first and second ends. For instance, a braid covering may be attached only at one end of the braid. Additionally, coils having complex shapes with secondary diameters are disclosed wherein opposite coil end portions may have different orientations when distally released from a compressed state within the cannula and delivery catheter lumens. For example, C-shaped coils, multiple loop coils, coils having both large and small secondary diameters, and "cloverleaf" configured coils are disclosed.

Another non-detachable vaso-occlusion coil that is pre-loaded in a uni-directional introducer cartridge for delivery is disclosed in U.S. Pat. No. 4,994,069 to Ritchart et al. Ritchart et al. discloses a coiled wire for use in small-vessel vaso-occlusion and having a convoluted space filling conformation when in a relaxed condition, a linear configuration when in a stretched condition, and a memory from the stretched to the relaxed condition when released from a delivery catheter into a vessel.

The preferred method of use disclosed in Ritchart et al. includes providing the vaso-occlusion wire in a prepackaged form in a sterile canula which is adapted to engage the proximal end of the delivery catheter. The canula is attached to the delivery catheter and the wire is transferred into the delivery catheter by a short wire, then advanced therethrough by a pusher. Various coil secondary configurations are described, wherein the coil shape is restrained within the pre-loaded canula and delivery catheter lumen prior to being discharged into a body space. The introducer cannula is not shown or described in detail.

Another example of an embolic coil that is pre-loaded in an introduction device as a cartridge is described in U.S. Pat. No. 5,382,260 to Dormandy et. al. The Dormandy '260 patent discloses a co-axial telescoping arrangement including a femoral artery sheath, a guiding catheter, and a coil delivery catheter. A C-shaped embolization device such as a coil is provided in an introducer cartridge made of clear transparent plastic such as a radiation sterilizable polycarbonate. A tubular member of the cartridge is bendable but relatively rigid so that it can be utilized as an introducer. A distal extremity of the cartridge is provided with a tapered tip and a hub is mounted on the proximal extremity, the hub also being formed of clear radiation sterilizable polycarbonate. The pre-loaded coil can thus be delivered only in one direction.

A pre-loaded tube for delivery of a vein-branch blocking member is also disclosed in U.S. Pat. No. 5,342,394 to Matsuno et al. Matsuno discloses an apparatus and method for blocking a vein branch comprising a vein-branch blocking member pushed out of a delivery tube with a push-out member and into the vein. The outer tube is bent and slidably receives an inner tube with a distal storing portion filled with a vein-branch blocking member. A push-out member pushes out the blocking member in the vein branch. The pre-loaded inner tube is flexible and has a proximal end that is fixed with a grip that is adapted to engage the proximal end of the outer tube in various embodiments. The distal shape of the outer tube is between 60 and 120 degrees and allows the inner tube to be easily inserted in the vein branch branching from the lateral wall of the vein. An embodiment discloses an articulation means for the distal bend, but no way to have a straight end if desired. The proximal end of the tube, however, is straight but is not adapted to be used distally nor is the distal shaped end adapted to straighten and be interchangeably used proximally.

Another pre-loaded cartridge/embolus supply system and method is disclosed in U.S. Pat. No. 5,133,731 to Butler et al. The Butler '731 patent discloses a magazine of cartridges pre-loaded with artificial emboli that are discharged therefrom into an embolus-delivery catheter coupled to a dispenser housing and inserted through a venotomy into a body space such as a blood vessel. The disclosed cartridges have an enlarged outlet head at the front end and a different enlarged inlet head at the rear end, each head abutting an opposite wall of the magazine. The emboli are pre-loaded at the factory in a central cartridge lumen so that it is ready to be discharged through the outlet head when it is later "hit"

during use by a slug of fluid expelled from a fluid supply assembly provided.

A hydraulic embolus delivery system and method using pre-loaded cartridges is disclosed by Butler et al. in U.S. Pat. No. 5,167,624. The Butler '624 patent discloses a hydraulic system for delivering an embolus from a pre-loaded cartridge coupled to the lumen of a delivery catheter. A benefit of alleviating the need for multiple pushers is described in the patent. The cartridge described in the Butler '624 patent has a passageway containing the pre-loaded coil in a stretched state, an inlet end to receive an injection stream of pressurized fluid from a source, and an outlet end through which the coil is discharged by way of the force imparted on the coil from the fluid injection. An alternative embodiment is disclosed having an inlet fitting at one end and an outlet mouth of the tubing at the other end for connecting to an introducer catheter. The fittings disclosed are of standard size and shape so that they mate easily with other attachment fittings.

A pre-loaded vaso-occlusion coil/introducer apparatus cartridge is also disclosed in pending U.S. patent application Ser. No. 08/413,970 for "Liquid Coils With Secondary Shape", filed Mar. 30, 1995. That document describes an occlusive implant having a pre-formed distal end and an extremely flexible proximal end. The coil is pre-loaded in an occlusive device cartridge or introducer. A sidearm adaptor fluidly couples the distal end of the cartridge to the proximal end of a delivery catheter. A syringe provides fluid flow to push the coil out of the cartridge, through the delivery catheter, and then out into the desired vessel site for occlusion. The pre-formed distal coil end has a greater flow resistance than the proximal portion of the coil such that the proximal coil portion desirably piles against the distal coil portion in a ball-like mass and engages a vessel wall for occlusion.

The cartridge includes a hub for receiving the discharge end of a syringe and a flexible elongated tubular member for discharging the occlusive device that is pre-packaged therein out of the tubular member and into the delivery catheter. The tubular member has a proximal end secured to a hub recess and a distal end adapted for being releasably secured within an inlet of the delivery catheter sidearm.

Various designs of vaso-occlusive coils are disclosed in U.S. Design patent application Ser. No. 29/037,001, filed Mar. 31, 1995 by Mariant et al. Several of these designs have differing secondary shapes at the opposite ends, for example wherein terminal ends of large loops of secondary helix shapes have different geometries due to the ends' orientation in relation to the handedness of the helix. As such, the space filling mechanisms may vary if one were to re-orient the direction that the shaped coils take when released from a stretched, confined state within an introducer and delivery tube lumen and into a less confined soft tissue space. However, when such coils are pre-loaded into known delivery cartridges their direction can not be re-oriented to vary the desired distal and proximal space filling geometries when released from a restraining delivery sheath. Existing uni-directional delivery cartridges don't allow for such re-orientation.

Thus, known delivery catheters such as microcatheters, infusion catheters, and introducer devices are uni-directional delivery devices having distinct and fixed proximal and distal ends. The particular design features in known delivery catheters, be them materials, dimensions, shapes, or orientation of housed implants, can be varied only by having multiple devices available that incorporate varying configurations. There is no known alternative to the uni-directional prior art in which the opposite ends of a catheter can be switched as distal and proximal ends in order to achieve varied catheter performance.

Most importantly, known vaso-occlusive coils can presently be delivered only uni-directionally because only uni-directional delivery catheters such as introducer cartridges are available. If a pre-loaded vaso-occlusion coil were desired to be delivered in a direction opposite its orientation within the cartridge with fixed distal and proximal ends, it would have to be removed and replaced in the desired orientation. Another solution to the problem would be to provide two coils in two uni-directional cartridges, one in each orientation—in other words to provide two devices, each having the coil pre-loaded in a cartridge in one of the two directions.

None of the references cited above provide a bi-directional catheter design that has two opposite ends that are adapted to interchangeably function as the catheter distal and proximal ends during use.

Nor do the references cited above provide a bi-directional catheter that is adapted for use as a single dilator device where both ends are adapted to be used for step-wise dilation of initial needle puncture sites in tissues to achieve relatively large-bore access diameters.

Nor do the references cited above provide a single bi-directional catheter that can facilitate the bi-directional delivery of implantable devices such as embolic coils that are pre-loaded in the catheter as a cartridge assembly.

The device features and related methods of the current invention provide solutions to these problems and more.

SUMMARY OF THE INVENTION

This invention is a bi-directional medical catheter device having an elongate body with two ends and two end portions, and an elongate body lumen extending between the ends. Each end portion is adapted to be interchangeably introduced as a distal catheter end into a delivery device lumen or body space and to engage a proximal coupler as a proximal catheter end.

The present invention is also a bi-directional medical catheter device having tapered ends with outwardly reducing outer diameters that terminate at the body ends.

The present invention is also a bi-directional medical catheter device having at least one coupler removably engaged with one of the catheter body end portions and being adapted for coupling the catheter device with a second device.

The present invention is also a bi-directional medical catheter device having a lumen extending from one end to the other and which is pre-loaded with an implantable device such as a vaso-occlusive coil. The catheter/implantable device combination forms a cartridge that is adapted for bi-directionally introducing the implantable device interchangeably through either of its end portions and then into a delivery device lumen or body space.

BRIEF DESCRIPTION OF THE DRAWINGS

FIGS. 5A and 5B show cut-away side views of two preferred configurations of the coupler embodiment of FIG. 4.

DETAILED DESCRIPTION OF THE INVENTION

Bi-Directional Catheter

The present invention is broadly a bi-directional catheter having an elongate body with two end portions adapted to be interchangeably inserted into a delivery device or body space as the catheter distal end or to be joined with a coupler as the catheter proximal end during use. Additionally, specific preferred embodiments that are herein disclosed include: (1) a catheter body configuration having two tapered end portions, (2) a bi-directional catheter body having at least one removably adapted coupler, and (3) a combination cartridge configuration made up of a bi-directional catheter that is pre-loaded with an implantable device, such as a vaso-occlusive coil.

With the embodiments specifically disclosed herein, the "bi-directional" ability of the present catheter invention provides a particular benefit in the bi-directional introduction of pre-loaded implantable object devices through a lumen of the catheter. With the present invention, such implantable devices may be implanted in one of two orientations or directions, depending upon the catheter end through which it is desirably delivered.

Figure 1:
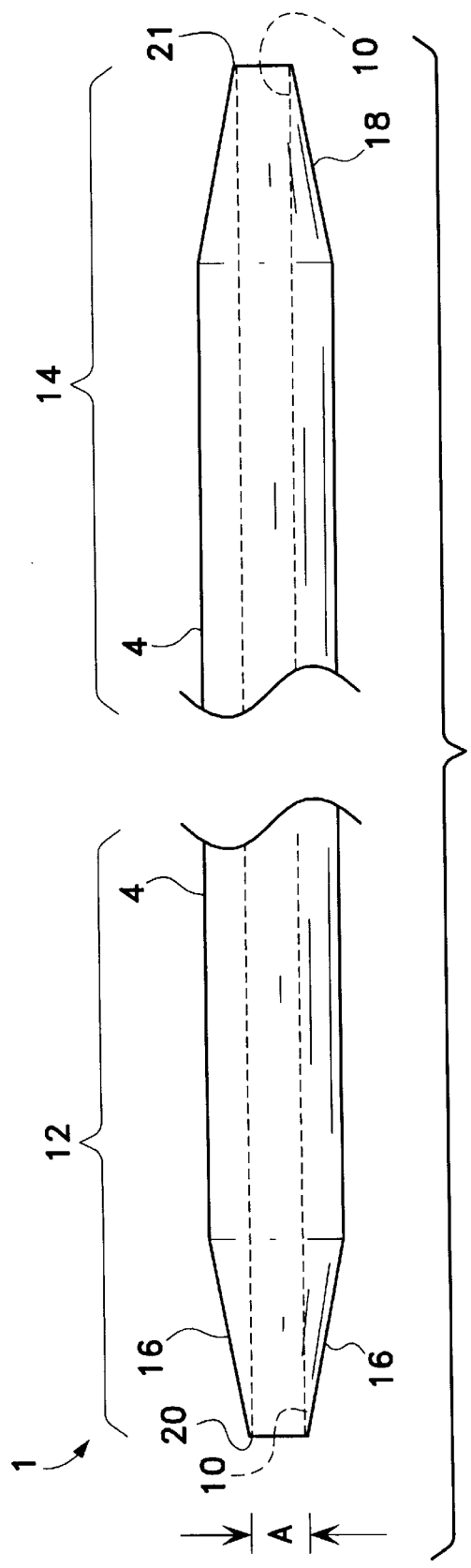
FIG. 1 shows an overall side view of a preferred bi-directional catheter of the present invention.

FIG. 1 shows a first preferred embodiment of the present invention. Catheter 1 is shown to have an elongate body 4 that forms a lumen 10 extending therethrough and has two end portions 12 and 14 that have tapers 16 and 18 that terminate with reduced outer diameters, or "entry profiles", at outer ends 20 and 21. Tapers 16 and 18 give the catheter a beneficial entry profile, shown for example in FIG. 1 as "A", to aid in inserting either end of the catheter 1 into a delivery device or body space. "Profile" is herein defined as the smallest size hole through which a given location or length of a component or device can fit. The tapers can be ground or sanded, molded, heat processed such as by heating and necking a section of tubing, or made in any other way known or obvious to those of ordinary skill.

Although the catheter end portions 12 and 14 of FIG. 1 can be interchangeably used as catheter distal or proximal ends, it is contemplated that the two end portions 12 and 14 can provide different benefits. For instance, it is contemplated that in the two taper design of FIG. 1, the shapes or dimensions of the tapers 16 and 18 may be different. Each shape or dimension may be more desirable for particular proximal or distal uses based upon variable medical or anatomical needs.

Similarly, each end portion may have other differentiating characteristics without losing the ability to be used interchangeably as a distal or proximal catheter end. One example of such a difference may be in the material chosen for each opposite end portion. For example, one end portion may be stiff and the opposite end portion may be more flexible, such that the interchangeability of the ends accommodates different anatomies or device uses. Or, one end portion may have a certain coating (e.g. heparin) that the other does not, such that the coated end would be interchangeably oriented proximally or distally to suit where the coating is desired.

Therefore, the range of materials chosen for a device utilizing the novel catheter design of the present invention is limited only by the intended use of the device. The available list of materials for construction of the catheter is constrained only by the performance requirements, such as flexibility and push transmission, required for the intended use. For example, the bi-directional design may be used as a distal delivery device such that the catheter distal end must be adapted for placement of object devices in distal, tortuous anatomy. Or, the novel design may be used as an introducer device to place an object device into only the proximal housing or lumen of another in-dwelling delivery device for distal placement therethrough. In any case, the materials chosen for construction of the components of catheter 1 can be any of those suited for standard devices currently being used in similar applications but without the bi-directional ability of the present invention.

Generally speaking, however, the most suitable materials for sections of body 4 ideally designed for remote distal uses are more flexible and would generally include low to medium density polyethylenes, and low durometer polyurethanes, polyolefin co-polymers, Nylons and polyesters. Materials generally suitable for more proximal uses are stiffer and include high density polyethylenes, high durometer polyurethanes, polyacrylates, polypropylenes, and polyimides.

Figure 2:
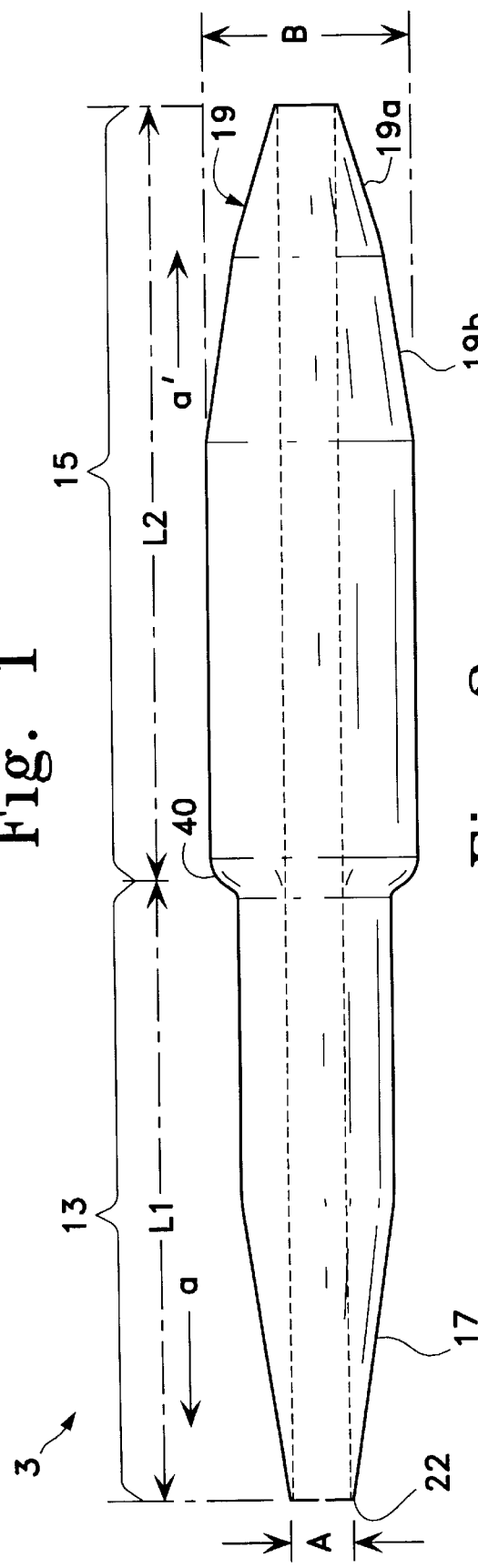
FIG. 2 shows an overview perspective of a preferred embodiment of the bi-directional catheter invention that is useable as a single dilator capable of two dilations, one each in two directions and at step-wise increasing profiles.

The bi-directional catheter of the present invention is shown at FIG. 2 as catheter 3 that is configured as a dilator useful in dilating an initial vessel puncture to larger hole diameters for vascular access. This dilator design allows for step-wise dilation of an initial access hole to a relatively larger hole in a preferred method over those possible when using previously known uni-directional dilator catheter designs.

Bi-Directional Dilator

The inventive bi-directional dilator shown in FIG. 2 eliminates the need for multiple dilators when such large access sites are desired. This is because the dilation can be done by interchanging the two end portions 13 and 15 and advancing the catheter in two directions for step-wise dilation.

Each end portion 13 and 15 has a different profile in the dilator embodiment of FIG. 2. End 22 has a first entry profile "A" and may be first introduced into the puncture hole, with the catheter end portion 13 being advanced in the direction shown in FIG. 2 as "a". Traversing taper 17 while advancing end portion 13 through the puncture site allows for the first-pass dilation of the access hole. Once the taper has been advanced completely past the puncture hole, or transition 40 is met, the first step dilation is completed. The dilator may be removed, turned in the opposite direction, and then re-advanced into and through the site, this time in direction "a'" relative to the dilator with end portion 15 being the dilator catheter distal end and end portion 13 being the catheter proximal end. Taper 19 is shown in FIG. 2 as having two taper regions 19a and 19b, 19a ending in a diameter closely approximating the profile of end portion 13 and 19b being dimensioned to dilate further to a desired, final hole diameter. Between the two dilation steps, the puncture site diameter is increased from at least "A" to at least "B". The farthest that the dilator is advanced into the anatomy is the longer length of the two end portions, either "L1" or "L2".

This is in stark contrast to the scenario where this step-wise dilation is instead done with a previously known uni-directional dilator catheter of corresponding dimensions. In that case, end portion 15 would be reverse-oriented relative to end portion 13 and taper 19 would be adjacent to end portion 13 instead of at an opposite end (not shown). The same dilation as previously described in a bi-directional application would now require an advancement length of up to "L1+L2", depending on the lengthwise contribution taper 19 makes to the overall length "L2".

Couplers Removably Adapted to Bi-Directional Catheter Ends

Figure 3A:
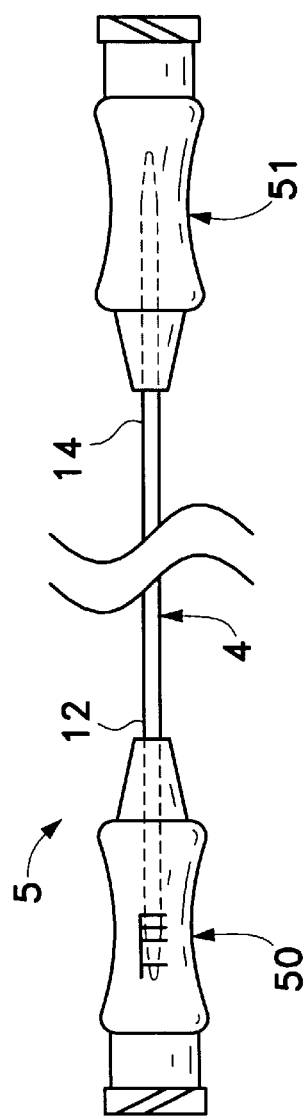
FIGS. 3A and 3B show two perspective views of a preferred embodiment of the bi-directional catheter invention, wherein couplers may be removably mounted on opposite catheter ends and adaptedly removed from the ends, respectively.
Figure 3B:
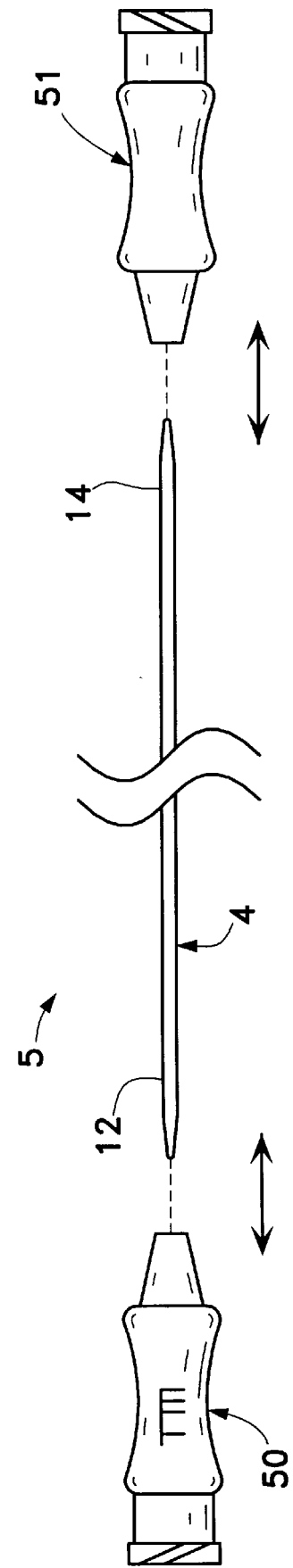

A further embodiment of the bi-directional catheter of the present invention is shown in FIGS. 3A and 3B as catheter 5. FIG. 3A shows catheter 5 additionally comprising at least one of couplers or adaptors 50 and 51 removably engaged with at least one of end portions 12 and 14, respectively. FIG. 3B alternatively shows each coupler 50 and 51 removed from end portions 12 and 14. Where one coupler is engaged with a first body end portion and the second coupler is removed from the second body end portion, it is contemplated that the second end portion is desirably used as the distal catheter end to be placed in a body space or co-axially within a delivery device lumen. In such a configuration, the first body end portion with the coupler engaged therewith is contemplated to be the opposite proximal end, the coupler being accessible to a physician for interfacing with other devices or receiving object devices into a lumen. The present invention, when incorporating removably engaged couplers, contemplates either having two couplers removably engaged on opposite catheter ends, or having one coupler which is adapted for removable engagement with at least one of the two catheter body ends.

Any design of coupler 50 or 51 capable of being removably engaged with at least one of catheter end portions 12 and 14 is contemplated as falling within the scope of the bi-directional catheter invention. One design of removably engaging couplers 50 and 51, however, is shown for example in a sectional view of preferred coupler 50 at FIG. 4. Coupler 50 is shown to preferably have two adjacent regions. The first coupler region 52 is a bi-directional catheter receiving region, and the second coupler region 72 is a second device receiving region.

Figure 4:
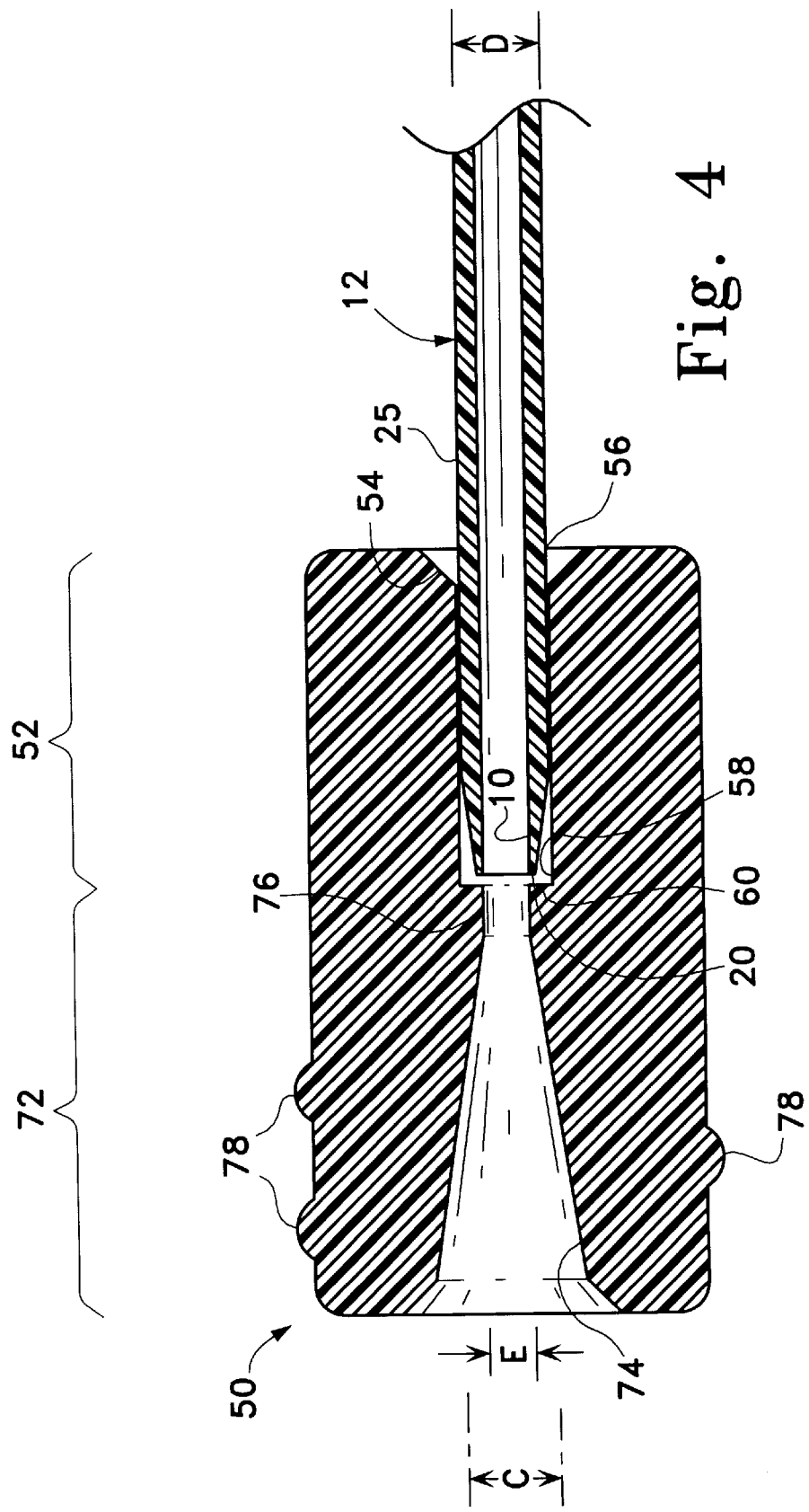
FIG. 4 shows a cut-away side view of a preferred coupler for the embodiment of FIGS. 3A and 3B.

As shown in FIG. 4, the first coupler region 52 includes a small funnel 54 for first encountering a catheter end and then directing the end and end portion. This is shown in FIG. 4 (by example) as funneling end 20 and end portion 12 into an elongated coupler lumen 56 having an inner diameter "C". The diameter "C" is limited in that end portion 12 must be removably fixed within coupler 50 by means of the engaging contact between end portion outer surface 25 and coupler lumen inner surface 58.

In one embodiment the coupler, such as for instance coupler 50, may be made of relatively elastic material, such as polyurethane, polyisoprene, polyvinyl chloride, styrene butadiene co-polymer, low density polyethylene, a rubber such as silicone rubber, or blends thereof. In such a case, the coupler lumen 56 inner diameter "C" may be equal to or less than end portion outer diameter "D". The ratio of these diameters, however, must allow for end portion 12 to be pressed into lumen 56 and up to stop 60, yet still allow for sufficient elastic force from the displaced lumen inner surface 58 to hold end portion 12 in removable engagement. The dimensions required for the two diameters "C" and "D" and the necessary corresponding ratio for meeting this performance requirement may vary depending on the materials chosen.

In another embodiment the coupler may be made of relatively inelastic material, such as polycarbonate, polyacrylate, mid to high density polyethylene, or blends thereof. Or, the inelastic material of the coupler may be a metal. When such an inelastic material is used, such a press fit as just described is not achievable without affecting the cross-section of the lumen of the catheter body end portion contained therein, especially for example when the body end portion is a simple extruded tube of relatively yieldable material. Desirably, an inelastic coupler would be dimensioned such that diameter "C" is equal to or slightly larger than "D". In this embodiment, end portion 12 may be inserted into coupler lumen 56 and be removably engaged therein by friction between the body end portion surface (25) and coupler lumen surface (58).

Another alternative embodiment of the current invention contemplates the removable coupler having an adjustable inner diameter. In this embodiment, the catheter end portion receiving portion of the coupler has a first inner diameter and is adapted to slidably receive the catheter end portion therein. Once the catheter end portion is so placed within the coupler, the coupler inner diameter is adjusted down onto the outer surface of the catheter end portion with a force to hold it therein. Such an adjustable inner diameter may be achieved for example through the use of a collet or an O-ring, together with a compressing member as may be contemplated by one of ordinary skill.

The second coupler region 72 of FIG. 4, or the second device receiving region, is preferably adapted for receiving a device such as a pusher or guidewire, and is preferably so adapted by incorporating a large funnel as is shown at 74. Large funnel 74 is adapted to receive a pusher or guide wire or other object device and direct the device into the elongate body lumen 10 at body end portion 12 located within first coupler region 52. The large funnel 74 has a first large funnel end 76 that is adjacent the first coupler region 52 and forms stop 60 for elongate body end portion 12. Large funnel end 76 has an inner diameter "E" that closely approximates the diameter of elongate body lumen 10 when body end portion 12 is removably engaged within first coupler region 52.

Thus, a relatively continuous surface is internally formed within coupler 50 when body end portion 12 is advanced into first region lumen 56 and against the adjacent large funnel end 76. This facilitates a relatively smooth introduction of an object device into elongate body lumen 10 within the preferred coupler 50.

Alternatively, large funnel end 76 may be designed with an inner diameter "E" that is slightly smaller than the diameter of lumen 10. In this configuration, introduction of object devices into lumen 10 through coupler 50 is further insured against a possibility of encountering a ridge at the elongate body end such as at 20. Additionally, this configuration may provide an additional stop to prevent passage of a device from lumen 10 proximally through coupler 50. For instance, a pre-loaded implant (not shown) in lumen 10 may be more safely housed therein when large funnel end 76 has inner diameter "E" smaller than the diameter of lumen 10.

Second coupler region 72 may also comprise a luer fitting that has threads for threadably engaging a coupler of a second device. The luer fitting can be either the male or female side of the two device adaption, and can have either outward threads, as shown at 78 in FIG. 4, or may be inwardly bevelled to accept outward threads of a mating device. Additionally or alternatively, large funnel 74 may also be adapted to frictionally engage a discharge end of a syringe as may be apparent to one of ordinary skill.

FIG. 5A shows a composite cross-sectional view of bi-directional catheter 7 with removable coupler 50 adapted to end portion 12. End portion 12 in FIG. 5A is the catheter proximal end and opposite end portion 14 thus becomes the catheter distal end. FIG. 5B alternatively shows a composite cross-sectional view of bi-directional catheter 7 with removable coupler 50 instead adapted to end portion 14. Here, the end portions are interchanged and end portion 14 is the catheter proximal end and end portion 12 is the catheter distal end. Thus, the catheter configurations of FIGS. 5A and 5B show an example of the bi-directional catheter having interchangeably transposable proximal and distal ends, based upon which end portion is desirably adapted with coupler 50.

Figure 6:
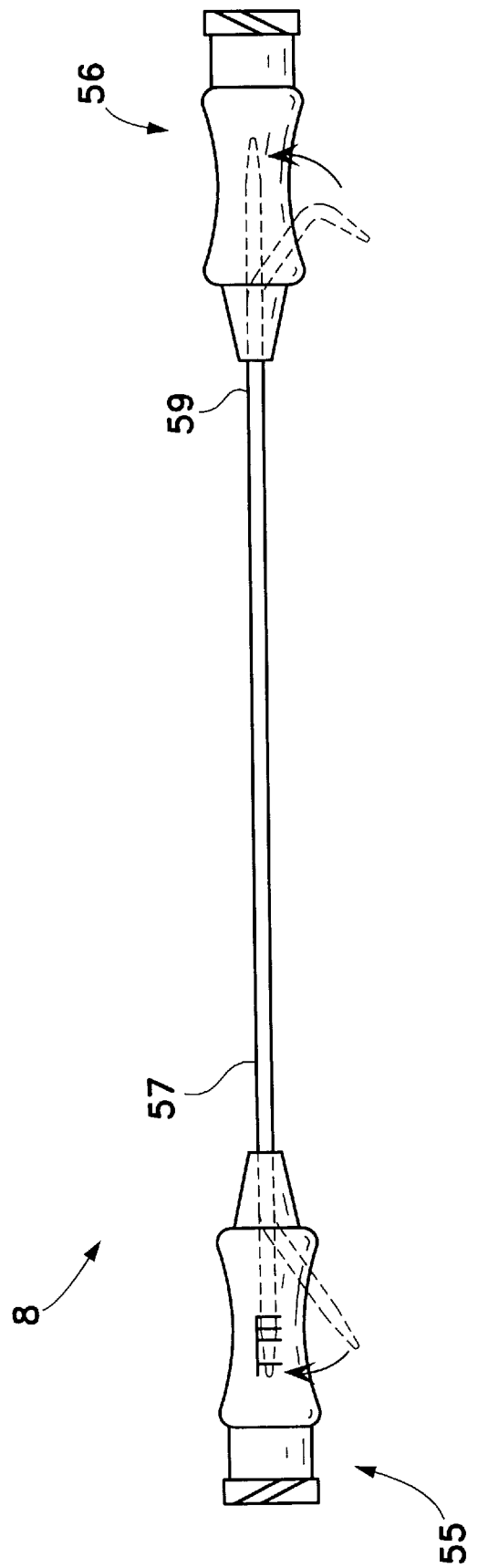
FIG. 6 shows an overview perspective of a preferred bi-directional catheter design with removably adapted coupler where each catheter body end portion has a shape that is straightened when adapted to the removable coupler.

FIG. 6 shows an additional embodiment of this invention at catheter 8. Removably adapted couplers 55 and 56 are shown in removable engagement with elongate body end portions 57 and 59, which have varying shapes. In this variation, end portion 57 has a first shape that is biased into a straight configuration within a lumen provided in coupler 55 when coupler 55 is placed over the first shape of end portion 57. End portion 59 is shown in FIG. 6 as having a second shape that may also be restrained into a straight configuration within a lumen of coupler 56 when coupler 56 is alternatively placed over this shaped portion. Both shapes of end portions 57 and 59 are shown in phantom in a first configuration when restrained within couplers 55 and 56, respectively, and in unrestrained configuration when the corresponding couplers are removed.

In using the embodiment of FIG. 6, one may select the elongate body end portion having the appropriate shape to be used as the catheter distal end and then place a coupler, for example coupler 55, over the opposite end portion. Alternatively, when two couplers are provided on the catheter body end portions, such as is shown in FIG. 6, one of the couplers may simply be removed from the end having the desired tip shape for use as the distal catheter end. The other coupler is merely left in place on the opposite end as the proximal coupler. Thus, either of the two shapes may be used distally in-vivo as desired and the proximal catheter end is maintained in a relatively straight condition where pre-shaped forms are not needed or desired.

Bi-Directional Cartridge with Pre-Loaded Implantable Device

Figure 7A:
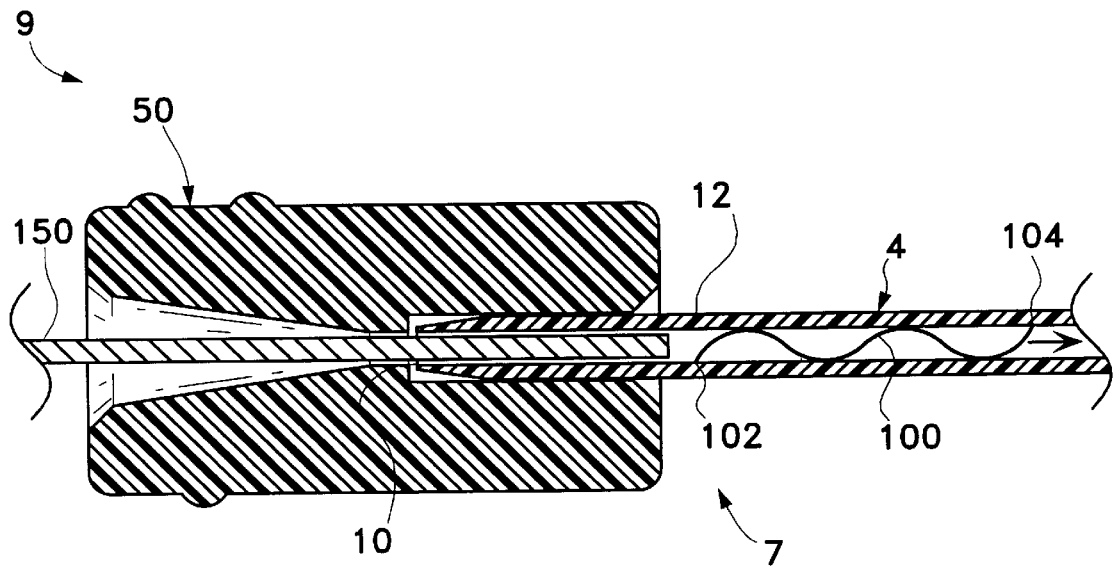
FIG. 7A shows a sectional side view of a preferred bi-directional catheter/implantable device cartridge embodiment where the implantable device is a type of vaso-occlusive coil.
Figure 7B:
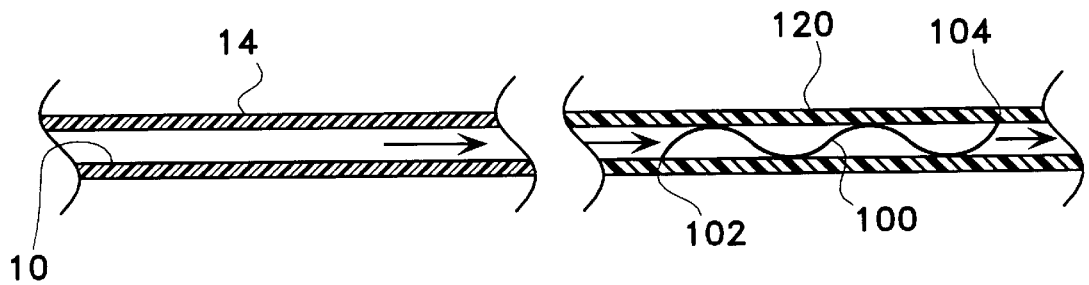
FIG. 7B shows a sectional side view of the vaso-occlusive coil of FIG. 7A after being pushed through the proximal and distal end portions of the cartridge and into a distal delivery catheter.
Figure 7C:
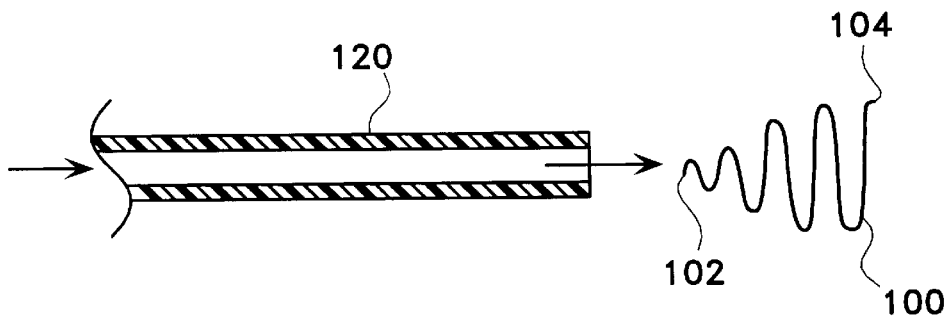
FIG. 7C shows a sectional side view of the vaso-occlusive coil after being pushed from the distal delivery catheter and into a body space.
Figure 8A:
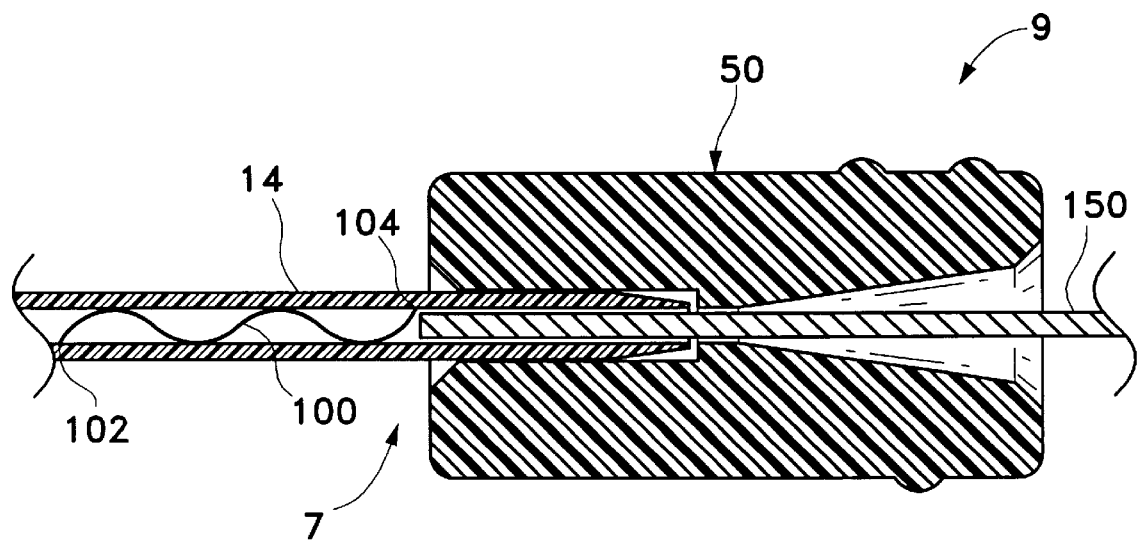
FIGS. 8A–C show sectional side views representing sequential steps of use for an alternative embodiment having a removable coupler adapted to an opposite cartridge body end portion than FIGS. 7A–C.
Figure 8B:
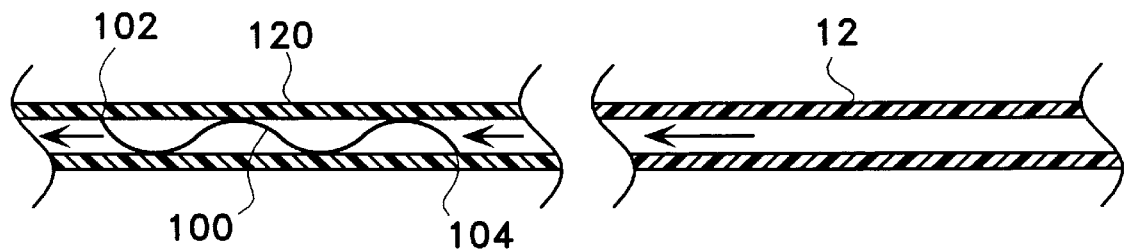
Figure 8C:
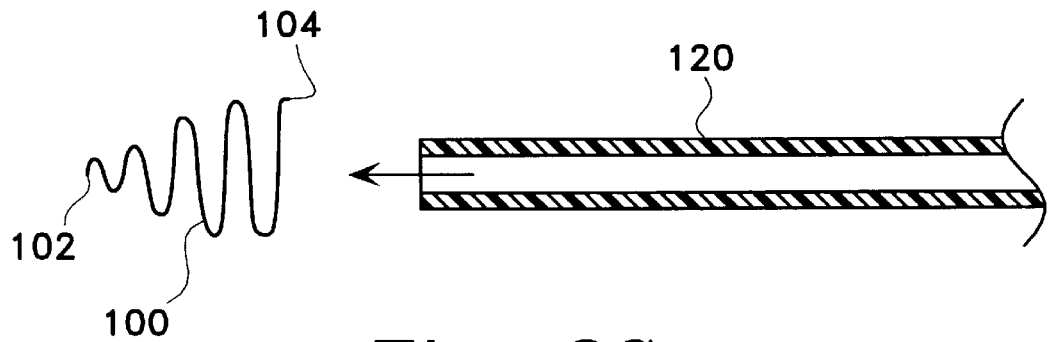

FIGS. 7A–C and 8A–C show alternative configurations of a preferred cartridge embodiment of the present invention at sequential steps in its use. FIGS. 7A–C show the use of the configuration to discharge a directional vaso-occlusive device from one end of the cartridge; FIGS. 8A–C show the use of the configuration to discharge a directional vaso-occlusive device from the other end of the preferred cartridge.

FIGS. 7A, 7B, and 7C show a preferred pre-loaded implantable device delivery cartridge embodiment at sequential steps in the use thereof. The preferred cartridge 9 comprises bi-directional catheter 7, which is shown in FIG. 7A by example to include elongate body 4 and proximal coupler 50, and an implantable device pre-loaded in elongate body lumen 10 of catheter 7. The implantable device is shown in FIGS. 7A–C by example as vaso-occlusion coil 100. A preferred vaso-occlusion kit includes the cartridge embodiment of cartridge 9 and further includes a pusher, shown in FIG. 7A at 150, and a distal delivery catheter, shown in FIG. 7B and FIG. 7C at 120.

FIG. 7A shows cartridge 9 as comprising removable coupler 50 adapted to end portion 12 of elongate body 4, with coil 100 disposed within elongate body lumen 10 in a preferred catheter/implantable device cartridge embodiment. While it is preferred to include the coupler adaption shown in FIG. 7A in operation of cartridge 9, inclusion of coupler 50 is not absolutely necessary, nor are other particular features shown for catheter 7 necessary. The present invention contemplates use of a pre-loaded bi-directional catheter as a vaso-occlusion coil cartridge without a coupler and without tapers at the opposite end portions. Any elongate catheter body that houses an implantable device in a lumen and that is adapted as a cartridge to distally deliver the implantable device through either of two opposite catheter ends is within the scope of the present invention.

As is shown in FIGS. 7A and 7B, adapting coupler 50 to end portion 12 creates a distal catheter end in end portion 14 through which coil 100 is to be discharged. Accordingly, coil 100, being pre-loaded in a fixed longitudinal orientation in lumen 10, becomes similarly oriented, with coil end 102 becoming the proximal coil end and coil end 104 becoming the distal coil end. The distal coil end is the leading end into the target body space when eventually coil 100 is discharged therein.

Coil 100 is shown in FIGS. 7A and 7B in a stretched condition, restrained from a radially expanded relaxed state, with the peaks of adjacent helix winds frictionally pressing against the inner wall of elongate body lumen 10. Eventually upon distal release of the coil into a larger diameter lumen, such as in a body space, the stretched coil preferably regains its relaxed memory such that expanded amplitude of its helical winds may engage a vessel wall and hold fixedly there during a thrombogenic response for occlusion.

FIG. 7B shows coil 100, still in a stretched configuration, after having been pushed preferably by pusher 150 (not shown) through distal end portion 14 and into a lumen of distal delivery catheter 120. Here, distal delivery catheter 120 is shown to have a similar inner lumenal diameter to that of elongate body lumen 10, such that the stretched condition of the coil is maintained until distal discharge therefrom into a body space.

Preferably, distal cartridge end portion 14 is co-axially received into a lumen of a proximal adaptor provided on distal delivery catheter 120, such that a smooth adaption between the two catheter lumens is maintained during advancement of the coil therethrough (adaption not shown). It is additionally contemplated, however, that distal delivery catheter 120 may have a different inner diameter than lumen 10 and still provide for efficacious distal delivery of the coil.

After transfer of the coil 100 from cartridge 9 into distal delivery catheter 120, FIG. 7C sequentially shows coil 100 after having been delivered longitudinally through distal delivery catheter 120 and discharged therefrom into a body space such as a vessel. Here, coil end 104 has a larger relaxed diameter than coil end 102 when released from the confines of the cartridge 9 and distal delivery catheter 120 lumens. As such, the adaption of coupler 50 to end portion 12 of this embodiment may be a desirable orientation when the larger expansion characteristics of coil end 104 are desirably at the distal, leading coil end when ejecting it into the body space, and when the smaller expansion of the coil end 102 are desirably at the trailing, proximal coil end.

FIGS. 8A, 8B, and 8C show an alternative coil delivery sequence where coupler 50 is instead adapted to the opposite end portion of the cartridge 9. Coupler 50 is shown in FIG. 8A (for example) adapted to end portion 14. The arrangement of FIG. 8A effectively switches the proximal-distal orientation of cartridge 9, allowing for the delivery of coil 100 in a direction that is in reverse orientation to that possible in the arrangement of FIG. 7A. FIG. 8A shows end portion 14 now being the proximal catheter end, wherein coil end portion 104 becomes the proximal coil end (as opposed to coil end 102 being proximal in the configuration of FIG. 7A). Similarly, end portion 12 is now the catheter distal end, through which coil 100 is discharged and into the distal delivery device lumen (shown in FIG. 8B). Finally, FIG. 8C shows that the coil is discharged from distal delivery device 120 and into the internal body space, but in the reverse orientation to the discharged coil of FIG. 7C. Here, the distal, leading coil end for desired space filling is the smaller diameter end 102, wherein the trailing end is the larger expanded proximal coil end 104.

Thus, the desired occlusion site for which the introducer cartridge configuration of FIGS. 8A–C is chosen may be something quite different than the occlusion sites more conducive to the implant orientation concomitant to the configuration shown in FIGS. 7A–C.

The present invention contemplates the use of any vaso-occlusive coil or implant disposed within a bi-directional catheter to form cartridge 9. However, as was just described, the embodiments of FIGS. 7A–C and 8A–C show coil 100 as having first and second coil ends 102 and 104 which have different properties. In those figures, coil 100 has coil ends 102 and 104 and has a secondary helical shape with a diameter which varies along the coils axis and between the coil ends. This type of coil has the optimal benefit of the present invention's ability to deliver the coil in two directions, one direction of which may have different space filling or other characteristics than delivery in the opposite direction.

Figure 9:
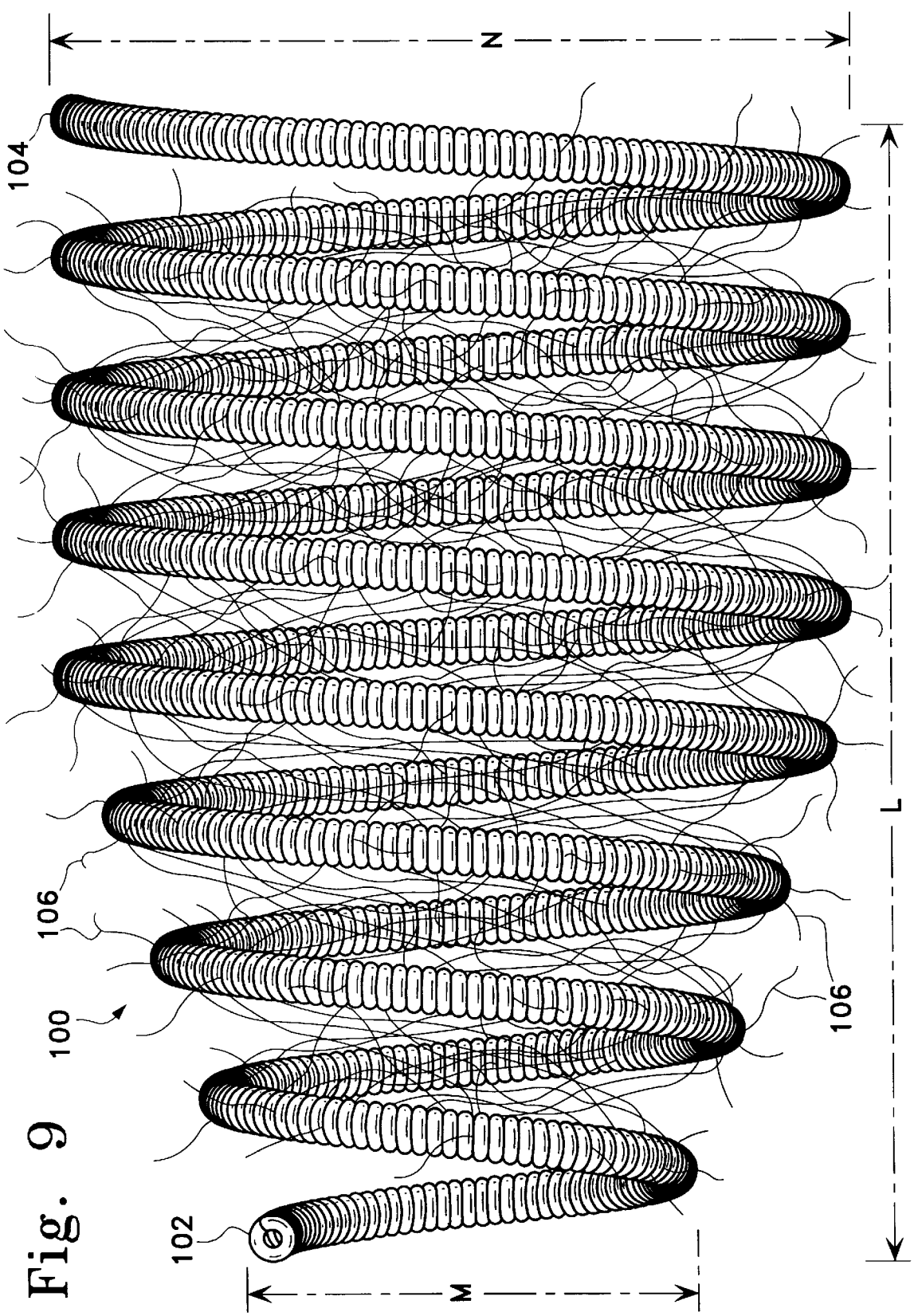
FIG. 9 shows a side perspective view of a preferred vaso-occlusion coil for use within the cartridge shown in FIGS. 7A–C or 8A–C.

An example of such a variable property vaso-occlusive coil that may be pre-loaded in the cartridge of the present invention is shown in detail in FIG. 9. Coil end 102 is shown to be the small diameter end of the coil, having representative diameter "M", wherein opposite coil end 104 is the wide coil end, having representative diameter shown as "N". FIG. 9 also shows an additional embodiment including thrombogenic fiber filaments 106 that extend from between adjacent coil turns of the primary helix. The fiber filaments 106 are of a thrombogenic material, preferably a polyester such as Dacron, and are believed to enhance the occlusion response to the vaso-occlusive coil.

The coil 100 shown in FIG. 9 is preferably constructed of metal wire filament having a diameter in the range of 0.0005" to 0.005", most preferably in the range of 0.001" to 0.0025". Preferably the metal is chosen from the group consisting of platinum, tungsten, stainless steel, nickle, titanium, iridium or alloys of these metals. Most preferably the wire is made of an alloy of 8% tungsten with the remainder being platinum. The wire may be wound into a primary helix over a mandrel. The resulting primary helix may have an outer diameter ranging from 0.005" to 0.035", preferably 0.010" to 0.035".

A secondary helix is imparted on the coil 100 by winding the primary helix onto a mandrel having a preferred secondary shape. The wire in the primary and secondary helix is then heat annealed to impart memory of the secondary helix to the metal. Additionally, fibers may be attached to the embolic coil to increase the thrombogenicity of the implant. For the type of coil 100 shown in FIG. 9, the dimension "M" is preferably in the range of 1 mm–4 mm, and the corresponding dimension "N" is preferably 2 mm–8 mm. Length "L" for coil 100 in FIG. 9 is preferably 20 mm–90 mm.

In addition to the shaped coil 100 just described, there are many other suitable examples of vaso-occlusive coil types to be pre-loaded in the catheter/implant cartridge of the present invention. Some of these are pushable and some are conducive to fluid delivery from the inventive cartridge. Such examples include the vaso-occlusive coils disclosed in the following patents or patent applications, all of which have been discussed above: pending U.S. Design patent application Ser. No. 29/037,001, filed Mar. 31, 1995, which discloses vaso-occlusive coils with varying secondary geometries; pending U.S. patent application Ser. No. 08/480,042, filed Jun. 06, 1995, which discloses coils having variable flexibility along their length and at their ends; and pending U.S. patent application Ser. No. 08/413,970, filed Mar. 30, 1995 which discloses hydraulically delivered coils having two opposite ends of varying flow resistance. These documents are herein incorporated in their entirety by reference.

The materials for catheter body 4 in the embodiment shown in FIGS. 7A–C and 8A–C may be chosen from well known materials as would be apparent to one of ordinary skill. However, one desirable material is clear polymeric material. This allows the attending physician to see the pre-loaded implant or coil within the elongate body lumen. The clear polymeric material may be polypropylene, polycarbonate, or other suitable polymers. Especially preferable is clear polymer polycarbonate. Alternatively, where a clear catheter body is not required or desired, other materials may be chosen. For instance, a metal hypotube may be used for catheter body 4.

In addition to a preferred embodiment comprising a clear polymer tubing for elongate body 4, removable coupler 50 may also be comprised of clear material to allow visualization of the interior channel therethrough.

The preferred use is shown sequentially in either sets of FIGS. 7A–C or 8A–C, with reference hereafter made to FIGS. 7A–C for purpose of example. The bi-directional catheter is pre-loaded with a coil to form an introducer cartridge for delivering the coil into another delivery device through which it is further transferred for implantation at a distally remote internal body location.

Before the coil is delivered from the pre-loaded cartridge and into the delivery device, a decision is made as to which orientation the coil is to be desirably introduced—in other words, which coil end will be distal and which coil end will be proximal. Some indicia would typically be provided for identifying which catheter end portion corresponds to which pre-loaded coil end.

One coupler may be adapted to be attached to one body end portion to make it the proximal catheter end, depending upon which direction the pre-loaded coil desirably is to be discharged. The opposite body end portion thus becomes the distal catheter end through which the coil is to be discharged from the cartridge. Where two couplers are provided on both body end portions, the coupler on the desired catheter distal end is removed. The proximal coupler may be attached or joined to a syringe and the body lumen that houses the coil may be filled with ringer's lactate or saline solution at low pressures, thereby purging lumen 10 of air.

The distal catheter end is then inserted into a delivery catheter 120 by opening a rotating hemostatic valve (not shown) located on the proximal end of the delivery catheter 120 and inserting the distal cartridge end into a lumen extending through delivery catheter 120. The delivery catheter 120 may be for example a microcatheter of the type described in U.S. Pat. No. 4,739,768 to Engelson, discussed above, which is incorporated in its entirety by reference.

Once the distal end of the cartridge 9 is placed within the proximal portion of delivery catheter 120, a pusher 150 is preferably introduced into the proximal cartridge coupler 50. A single pusher can be used to push the coil out of the introducer cartridge, through the delivery device 120, and out into the desired occlusion site. Or, alternatively, a series of pushers can be used. For instance, a plunger that is relatively short and easy to manipulate may be used to push the coil out of introducer cartridge 9 and into delivery device 120. A second pusher may then be used for delivering the coil through delivery device 120 and into distal anatomy. Any object device capable of performing the pusher functions herein described is contemplated as within the scope of the invention.

One example of a pusher that may be used in the present invention is described in issued U.S. Pat. No. 4,994,069 to Ritchart et al. Ritchart describes a pusher having a preferably stiff and straightened stainless steel proximal portion of constant diameter, and a distal portion comprising a tapered wire and a low-friction polymer tubing. A preferred pusher may have an outer diameter of approximately 0.010"–0.0161" and length ranging from 175–195 cm.

Once the distal end of pusher 150 is introduced into the cartridge 9 through the proximal coupler 50, it is then advanced through the cartridge elongate body lumen 10 and is further advanced to push the coil out of the cartridge 9, through the delivery device lumen, and out the delivery device distal end at the desired implant site and in the desired coil orientation.

Alternatively, fluid pressure or flow may provide the mechanism for delivering a vaso-occlusive implant from the cartridge of the present invention. Procedures similar to those disclosed in U.S. Pat. No. 5,167,624 to Butler et al (discussed above), which is herein incorporated in its entirety by reference thereto, and U.S. patent application Ser. No. 08/413,970 (also discussed above), filed Mar. 30, 1995, may be suitable, depending on the particular coils used and distal placement needs through the distal lumen of a microcatheter provided. The disclosure of the pending '970 application has been incorporated into this specification by reference thereto above.

Figure 10:
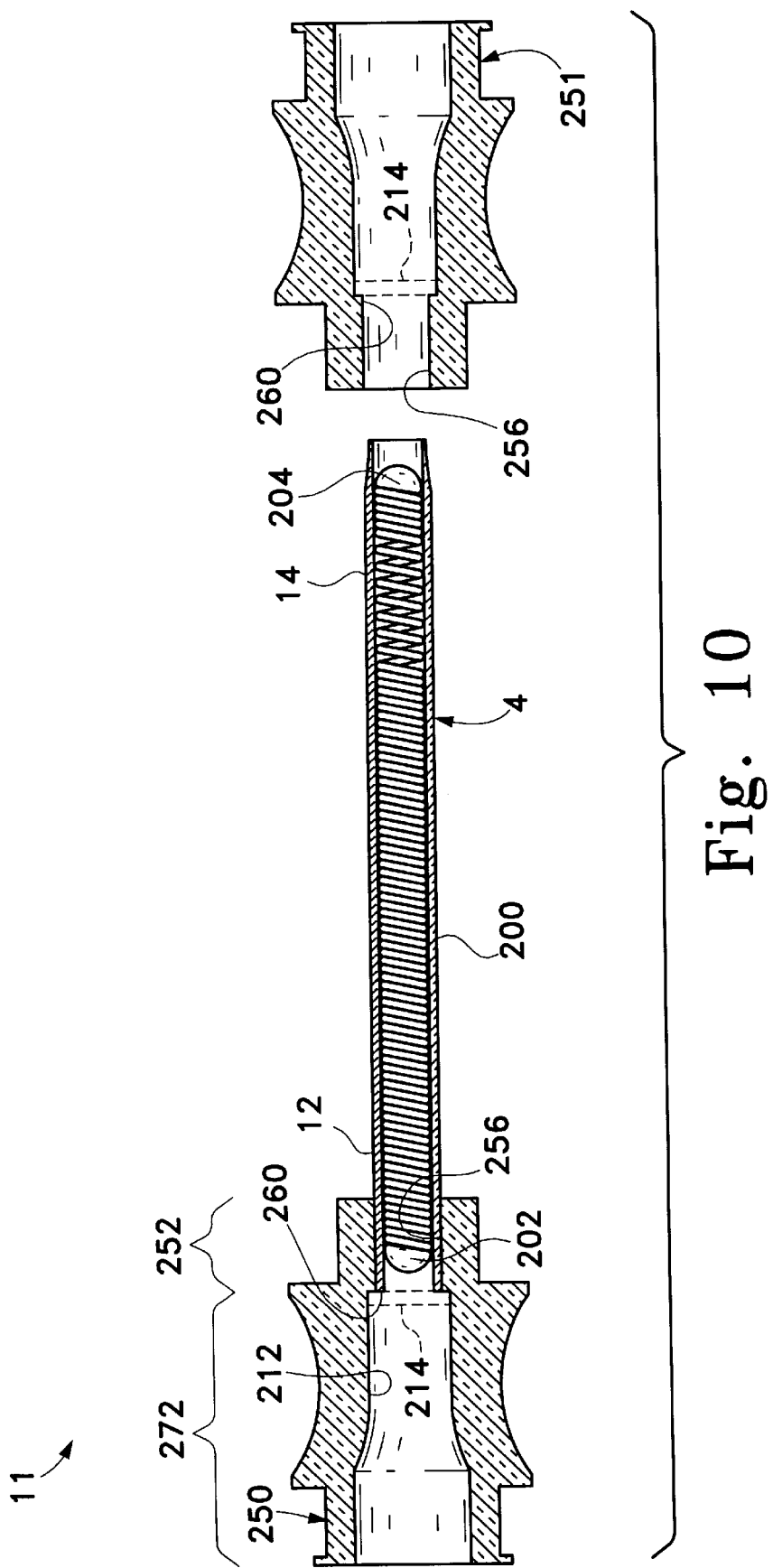
FIG. 10 shows a sectional side view of an alternative catheter/implantable device cartridge embodiment adapted with a novel removable hub for fluid delivery of the implantable device.

An alternative embodiment of the present invention is shown at pre-loaded catheter/implantable device cartridge 11 in FIG. 10. Cartridge 11 incorporates the novel fluid flow coil delivery cartridge of reference U.S. patent application Ser. No. 08/413,970, filed Mar. 31, 1995 into the current bi-directional catheter invention. Where FIGS. 7A–C and 8A–C show a coupler 50 adapted to slidably receive a pusher through funnel 74 and into elongate body lumen 10, FIG. 10 shows an alternative removable coupler designed specifically for fluid delivery of coil 200 from cartridge 11. The fluid delivery coupler is shown at 250 removably adapted to elongate body end portion 12 and representatively at 251 removed from elongate body end portion 14.

Coupler 250 in FIG. 10 is shown to have first coupler region 252 and second coupler region 272. First coupler region 252 is adapted to receive and removably engage either of the two body end portions 12 or 14 within first coupler lumen 256 in a coupling similar to that earlier disclosed in reference to FIG. 4. In a further embodiment, coupler 250 comprises a stop against which end portion 12 may rest within first coupler lumen 256 (not shown).

Second coupler region 272 has a recess 212 for housing a porous membrane or filter, shown in phantom at 214. Porous filter 214 permits working fluid (which preferably is a saline solution) to be discharged therethrough for impelling coil 200 through the catheter cartridge while preventing the coil 200 from backing into coupler 250. Once adapted to one of the end portions, the discharge end of a syringe (not shown) may be frictionally engaged within second coupler region 272. The cartridge may desirably be purged of air before use by infusing fluid at low pressure through porous filter 214. Subsequent fluid injections through filter 214 force coil 200 out the distal cartridge end opposite coupler 250, through a distal delivery catheter, and then exteriorly into a body space.

While one particular design for coil 200 is shown in FIG. 10, this serves only as an exemplary description in the figure. It is contemplated that any implantable device capable of fluid delivery through the bi-directional cartridge as described falls within the scope of the present invention. Also, additional features and methods of using the fluid delivery cartridge 11 of FIG. 10 for delivering vaso-occlusive coils, as for example may be described in the references cited above, are contemplated within the scope of this invention as would be apparent to one of ordinary skill.

The above is a detailed description of particular embodiments for the invention. Any combination of the disclosed embodiments is contemplated as within the scope of the present invention. It is also recognized that departures from the disclosed embodiments may be made and obvious modifications will occur to a person skilled in the art without departing from scope of the invention.

We claim as our invention:

1. A medical catheter assembly, comprising:
    an elongate body having first and second end portions, a cylindrical section between those end portions, said first and second portions being integral with said elongate body, and said elongate body defining an elongate body lumen having a body lumen diameter and extending between said first and second end portions,
    each of said end portions being removably introduceable into a delivery device lumen and a body space, and also to interchangeably engage a proximal coupler; and
    at least one coupler having a first coupler region that includes a first coupler lumen with a first coupler lumen diameter that will coaxially receive and removably engage at least one of said first and second end portions,
    said at least one coupler also having a second coupler region adjacent said first coupler region and including a second coupler lumen with a second coupler lumen diameter, said second coupler lumen diameter being larger than the body lumen diameter and being slidably accepting an object device and direct said object device into said lumen elongate body.

2. A medical catheter assembly as described in claim 1, wherein said at least one coupler will interchangeably engage with both of said first and second portions.

3. A medical catheter assembly as described in claim 1, further comprising:

exactly two said couplers, each of said couplers being removably at least one of said first and second end portions.

4. A medical catheter assembly as described in claim 1, wherein said first coupler region further comprises an elastic material;

said first coupler region has an umcompressed state such that said first coupler lumen is in an open position and such that said first coupler lumen diameter slidably receives at least one of said first and second end portions; and wherein said first coupler region is compressible to a compressed state such that said first coupler lumen is in a closed position and such that said first coupler lumen diameter is reduced to impart a force onto and removably engage at least one of said first and second end portions.

5. A medical catheter assembly as described in claim 4, wherein said first coupler region contains a compressible "O"-shaped ring.

6. A medical catheter assembly as described in claim 4, wherein said first coupler region contains a collet.

7. A medical catheter assembly as described in claim 1, wherein at least one of said first and second end portions has an outer profile;

said second coupler lumen terminates opposite said first coupler lumen in an outwardly tapered funnel opening; and wherein said funnel opening, said second coupler lumen, and said first coupler lumen form a channel extending through said coupler.

8. A medical catheter assembly as described in claim 7, wherein said first coupler inner diameter is larger than said outer profile and receives at least one of said first and second end portions and removably engages it therein with a friction fit.

9. A medical catheter assembly as described in claim 8, wherein said at least one coupler comprises a relatively inelastic material which is chosen from the group consisting of polycarbonate, polyacrylate, polyethylene, and blends thereof, and metal.

10. A medical catheter assembly as described in claim 7, wherein said first coupler lumen inner diameter is smaller than said outer profile and wherein said coupler further comprises an elastic material removably receiving at least one of said first and second end portions and removably engage it therein with a press fit.

11. A medical catheter assembly as described in claim 10, wherein said elastic material is chosen from the group consisting of polyisoprene, polyurethane, polyvinyl chloride, styrene butadiene co-polymer, silicone, and blends thereof.

12. The medical catheter assembly of claim 7, wherein said first coupler lumen diameter is larger than said outer profile and removably receives and engages at least one of said first and second end portions with a friction fit.

13. A medical catheter assembly as described in claim 1, wherein said at least one coupler comprises a luer adapter.

14. The medical catheter assembly of claim 1, wherein said at least one coupler comprises a relatively inelastic material is chosen from the group consisting of polycarbonate, polyacrylate, polyethylene, and blends thereof, and metal.

15. The medical catheter assembly of claim 1, wherein said first coupler lumen diameter is smaller than said outer profile and wherein said coupler comprises an elastic material that removably receives and engages at least one of said first and second end portions with a press fit.

16. The medical catheter assembly of claim 15, wherein said elastic material is chosen from the group consisting of polyisoprene, polyurethane, polyvinyl chloride, styrene butadiene co-polymer, silicone, and blends thereof.

* * * * *